United States Patent [19]

Beregi et al.

[11] Patent Number: 4,505,921
[45] Date of Patent: Mar. 19, 1985

[54] SULFONYLUREA COMPOUNDS AND THEIR USE IN TREATING DIABETES

[75] Inventors: Laszlo Beregi, Boulogne Billancourt; Pierre Hugon, Rueil Malmaison; Jacques Duhault, Croissy-sur-Seine; Michelle Boulanger, Marly le Roi, all of France

[73] Assignee: ADIR, S.A.R.L., Neuilly-sur-Seine, France

[21] Appl. No.: 529,735

[22] Filed: Sep. 6, 1983

[30] Foreign Application Priority Data

Sep. 23, 1982 [FR] France ................. 82 16012

[51] Int. Cl.³ ............... A61K 31/395; C07D 519/00
[52] U.S. Cl. ..................... 514/212; 546/194; 546/198; 546/201; 546/273; 546/270; 548/430; 548/454; 548/455; 548/465; 548/466; 548/472; 514/318; 514/323; 514/339; 514/414; 514/416; 514/417; 514/866
[58] Field of Search ............... 546/194, 201, 270, 273, 546/198; 548/430, 454, 455, 465, 466, 472; 424/274, 263, 267

[56] References Cited

U.S. PATENT DOCUMENTS 3,879,418  4/1973  Houlihan et al. .................. 548/454

FOREIGN PATENT DOCUMENTS 273153  8/1969  Austria ............................ 548/472

*Primary Examiner*—Robert T. Bond
*Attorney, Agent, or Firm*—Gordon W. Hueschen

[57] ABSTRACT

New sulfonylurea compounds of the formula:

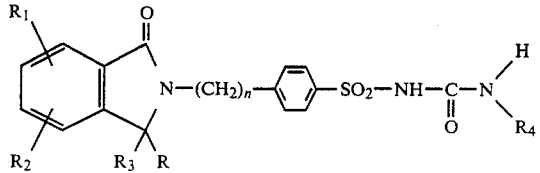

in which
n is 1 or 2,
R is thienyl, furyl, pyridyl or phenyl optionally mono or disubstituted,
$R_1$ and $R_2$, the same or different, each are hydrogen, halogen, ($C_1$ to $C_5$)-alkyl, ($C_1$ to $C_5$)-alkoxy, or trifluoromethyl, or together represent —CH$_2$—O—CH$_2$—,
$R_3$ is hydrogen, or hydroxy, and
$R_4$ is ($C_1$ to $C_5$)-alkyl, ($C_3$ to $C_8$)-cycloalkyl or azacycloalkyl of the formula:

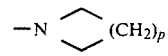

in which p is zero or an integer from 1 to 5, or azabicycloalkyl of the formula:

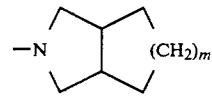

in which m is 1, 2, or 3.

These new compounds and physiologically tolerable salts thereof may be used as medicines especially in the treatment of diabetes.

6 Claims, No Drawings

SULFONYLUREA COMPOUNDS AND THEIR USE IN TREATING DIABETES

The present invention provides new sulfonylurea compounds of the formula I:

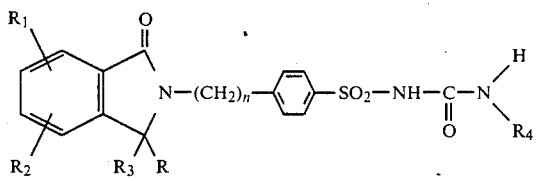
(I)

in which
n is selected from the group consisting of the integers 1 and 2;
R is selected from the group consisting of: thienyl, furyl, pyridyl radicals and the radical of the formula:

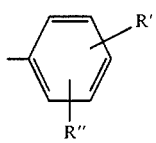

in which R' and R" which are the same or different are each selected from the group consisting of a hydrogen atom, halogen atoms, such as, for example, chlorine, fluorine and bromine atoms, a hydroxy radical, alkyl and alkoxy radicals each having from 1 to 4 carbon atoms inclusive, a trifluoromethyl radical and R' and R" together form a —CH$_2$—O—CH$_2$— group;
R$_1$ and R$_2$ which are the same or different are each selected from the group consisting of a hydrogen atom, halogen atoms, such as, for example, chlorine, fluorine and bromine, alkyl and alkoxy radicals each having from 1 to 5 carbon atoms inclusive and a trifluoromethyl radical, and R$_1$ and R$_2$ together form a —CH$_2$—O—CH$_2$— group;
R$_3$ is selected from the group consisting of a hydrogen atom and a hydroxy radical, and
R$_4$ is selected from the group consisting of alkyl radicals each having from 1 to 5 carbon atoms, cycloalkyl radicals having from 3 to 8 carbon atoms, azacycloalkyl radicals of the formula:

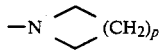

in which p is selected from the group consisting of zero and the integers from 1 to 5,
and azabicycloalkyl radicals of the formula:

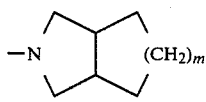

in which m is selected from the group consisting of 1, 2 and 3.

The present invention also provides a process for the preparation of the compounds of the formula I characterised in that the benzoic acids of the general formula II:

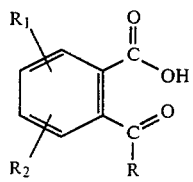
(II)

in which R, R$_1$ and R$_2$ have the meanings defined above, are treated with SOCl$_2$ in order to obtain the isobenzofuranones of the general formula III

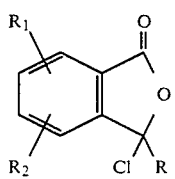
(III)

which are condensed with the compound of the general formula IV

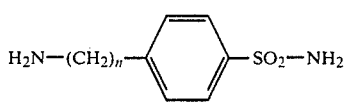
(IV)

in which n has the meaning given above, to obtain the 3-hydroxyisoindolones of the general formula V

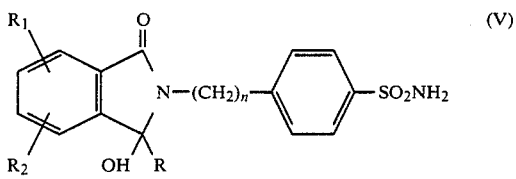
(V)

in which R, R$_1$, R$_2$ and n have the meanings given above, and these compounds (V) are:
condensed with a compound of the general formula VI

R'$_4$—N=C=O        (VI)

in which R'$_4$ represents an alkyl radical having from 1 to 5 carbon atoms or a cycloalkyl radical having from 3 to 8 carbon atoms,
to obtain derivatives of the general formula I'$_a$

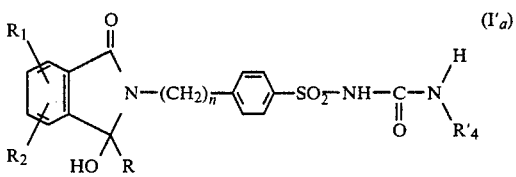
(I'$_a$)

in which R, R$_1$, R$_2$, n and R'$_4$ have the meanings given above; or
condensed with a compound of the general formula VII

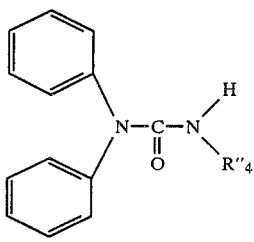

in which R″₄ represents an azacycloalkyl radical of the formula

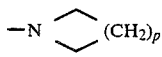

in which p has the meaning given above, or represents an azabicycloalkyl radical of the formula

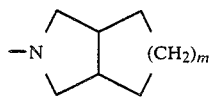

in which m has the meaning given above,
to obtain derivatives of the general formula I″ₐ

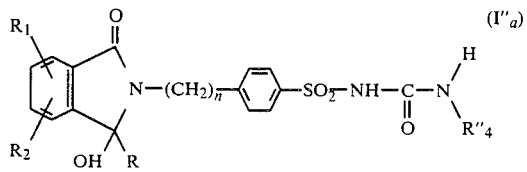

in which R, R₁, R₂, n and R″₄ have the meanings given above;
or
converted into isoindolones of the general formula VIII

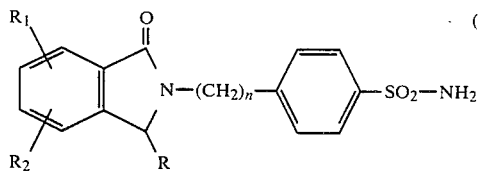

in which R, R₁, R₂ and n have the meanings given above,
and these isoindolones are condensed with a compound of the formula VI as defined above,
to obtain derivatives of the general formula I′ᵦ

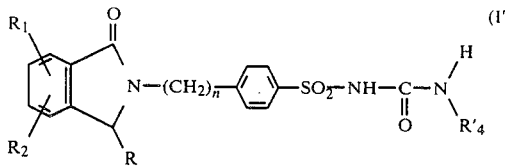

in which R, R₁, R₂, n and R′₄ have the meanings given above;

or
condensed with a compound of the general formula VII as defined above,
to obtain derivatives of the general formula I″ᵦ

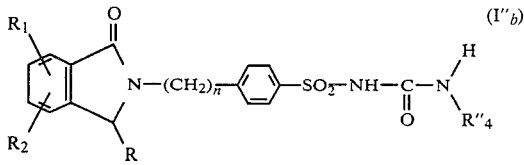

in which R, R₁, R₂, n and R″₄ have the meanings given above.

It will be noted that the group of compounds of the formulae I′ₐ, I″ₐ, I′ᵦ and I″ᵦ form the group of compounds of the formula I.

The present invention relates also to the salts formed with alkali metal or alkaline earth metal hydroxides, with alkali metal or alkaline earth metal carbonates and with alkali metal bicarbonates.

The derivatives of the general formula I and the physiologically tolerable salts thereof have interesting therapeutic properties, in particular a striking hypoglycaemic activity. They can therefore be used as orally administrable active medicaments for the treatment of diabetes.

Their toxicity is very low and the LD₅₀ studied in mice is greater than 3 g/kg per os for all the derivatives.

The hypoglycaemic activity was studied in rabbits and rats by the oral route. The minimum active dose is within the range of from 1 to 10 mg/kg and a reduction of 30% in the glycaemia is achieved with most of the derivatives using doses varying between 1 and 25 mg/kg.

By way of comparison, chlorpropamide, a well-known hypoglycaemic agent, would have to be administered to rats at the dose of 50 mg/kg in order to achieve the same effect. On the other hand, the LD₅₀ of that product is 1 g/kg; it is therefore 3 times more toxic than the derivatives of the present invention.

These new derivatives may be administered to diabetics in different pharmaceutical forms, preferably in the form of tablets, dragées, capsules or soft gelatin capsules for oral administration, in combination with suitable pharmaceutical carriers such as, for example, talc, starch, lactose or magnesium stearate. The doses used may vary within the range of from 2.5 to 100 mg, and preferably from 5 to 30 mg, per day.

The present invention also provides the pharmaceutical compositions containing as active ingredient a derivative of the formula I or a physiologically tolerable salt thereof, in admixture or conjunction with a pharmaceutically suitable carrier.

The following Examples, which are not limiting, illustrate the invention. All parts are expressed as parts by weight and the melting points are determined by the Kofler method.

EXAMPLE 1

3-chloro-3-phenyl-1-(3H)-isobenzofuranone

Over a period of 15 minutes, 22.5 parts of 2-benzoylbenzoic acid are added, in small portions, while stirring, to 40 parts of thionyl chloride. The reaction mixture is then brought slowly to reflux and this is maintained for 90 minutes. The excess thionyl chloride is removed in vacuo and the residue is taken up in 50 parts of anhydrous benzene and the whole is then evaporated to dryness in vacuo. The operation is repeated a second time and then the residue is taken up in 80 parts of anhydrous tetrahydrofuran. This solution is used in that form in the stage described below.

EXAMPLES 2 TO 11

The following derivatives were prepared according to the method described in Example 1:

(2) 3-chloro-3-(para-fluorophenyl)-1-(3H)-isobenzofuranone, starting from 2-(para-fluorobenzoyl)-benzoic acid.

(3) 3-chloro-3-phenyl-5-bromo-1-(3H)-isobenzofuranone, starting from 2-benzoyl-4-bromobenzoic acid.

(4) 3-chloro-3-phenyl-5,6-dimethoxy-1-(3H)-isobenzofuranone, starting from 2-benzoyl-4,5-dimethoxybenzoic acid.

(5) 3-chloro-3-(2-thienyl)-2-(3H)-isobenzofuranone, starting from 2-(2-thienoyl)-benzoic acid.

(6) 3-chloro-3-phenyl-5-methoxy-1-(3H)-isobenzofuranone, starting from 2-benzoyl-4-methoxybenzoic acid.

(7) 3-chloro-3-phenyl-5,6-methylenedioxy-1-(3H)-isobenzofuranone, starting from 2-benzoyl-4,5-methylenedioxybenzoic acid.

(8) 3-chloro-3-(meta-trifluoromethylphenyl)-1-(3H)-isobenzofuranone, starting from 2-(meta-trifluoromethylbenzoyl)benzoic acid.

(9) 3-chloro-3-(para-chlorophenyl)-1-(3H)-isobenzofuranone, starting from 2-(para-chlorobenzoyl)benzoic acid.

(10) 3-chloro-3-(meta-fluorophenyl)-1-(3H)-isobenzofuranone, starting from 2-(meta-fluorobenzoyl)benzoic acid.

(11) 3-chloro-3-(ortho-fluorophenyl)-1-(3H)-isobenzofuranone, starting from 2-(ortho-fluorobenzoyl)-benzoic acid.

EXAMPLE 12 para-[$\beta$-(2,3-dihydro-3-hydroxy-3-phenyl-(1H)-isoindol-1-on-2-yl)ethyl]benzenesulphonamide 12.35 parts of 3-chloro-3-phenyl-1-(3H)-isobenzofuranone in solution in 40 parts of anhydrous tetrahydrofuran are added, while stirring, over a period of approximately 15 minutes, to a solution of 10 parts of para-($\beta$-aminoethyl)benzenesulphonamide and 5.06 parts of triethylamine in 80 parts of anhydrous dimethylformamide. The temperature rises from 25° to 50° C. and after being stirred for 2 hours the reaction mixture is diluted in 400 parts of water. The precipitate formed is suction-filtered and dried in air and then recrystallized in 360 parts of isopropanol. 12 parts of para-[$\beta$-(2,3-dihydro-3-hydroxy-3-phenyl-(1H)-isoindol-1-on-2-yl)ethyl]benzenesulphonamide are obtained melting at 225° C.

EXAMPLES 13 TO 23

The following derivatives were prepared according to the method described in Example 12:

(13) para-[$\beta$-(2,3-dihydro-3-hydroxy-3-(para-fluorophenyl)-(1H)-isoindol-1-on-2-yl)ethyl]benzenesulphonamide, m.p.: 231°–232° C. (isopropanol), starting from 3-chloro-3-(para-fluorophenyl)-1-(3H)-isobenzofuranone and para-($\beta$-aminoethylbenzenesulphonamide.

(14) para-[$\beta$-(2,3-dihydro-3-hydroxy-3-phenyl-5-bromo-(1H)-isoindol-1-on-2-yl)ethyl]benzenesulphonamide, m.p.: 248°–250° C. (ethanol), starting from 3-chloro-3-phenyl-5-bromo-1-(3H)-isobenzofuranone and para-($\beta$-aminoethyl)-benzenesulphonamide.

(15) para-[$\beta$-(2,3-dihydro-3-hydroxy-5,6-dimethoxy-(1H)-isoindol-1-on-2-yl(ethyl]benzenesulphonamide, m.p.: 225° C. (acetonitrile), starting from 3-chloro-3-phenyl-5,6-dimethyoxy-1-(3H)-isobenzofuranone and para-($\beta$-aminoethyl)benzenesulphonamide.

(16) para-{$\beta$-[2,3-dihydro-3-hydroxy-3-(2-thienyl)-(1H)-isoindol-1-on-2-yl]ethyl}benzenesulphonamide, m.p.: 188° C. (acetonitrile), starting from 3-chloro-3-(2-thienyl)-1-(3H)-isobenzofuranone and para-($\beta$-aminoethyl)benzenesulphonamide.

(17) para-[$\beta$-(2,3-dihydro-3-hydroxy-3-phenyl-5-methoxy-(1H)-isoindol-1-on-2-yl)ethyl]benzenesulphonamide m.p.: 193°–194° C. (isopropanol), starting from 3-chloro-3-phenyl-5-methoxy-1-(3H)-isobenzofuranone and para-($\beta$-aminoethyl)benzenesulphonamide.

(18) para-[$\beta$-(2,3-dihydro-3-hydroxy-3-phenyl-5,6-methylenedioxy-(1H)-isoindol-1-on-2-yl)ethyl]benzenesulphonamide, m.p.: 216°–218° C. (ethanol) starting from 3-chloro-3-phenyl-5,6-methylenedioxy-1-(3H)-isobenzofuranone and para-($\beta$-aminoethyl)benzenesulphonamide.

(19) para-[$\beta$-(2,3-dihydro-3-hydroxy-3-(meta-fluorophenyl)-(1H)-isoindol-1-on-2-yl)ethyl]benzenesulphonamide m.p.: 234°–236° C. (ethanol), starting from 3-chloro-3-(meta-fluorophenyl)-1-(3H)-isobenzofuranone and para-($\beta$-aminoethyl)benzenesulphonamide.

(20) para-[$\beta$-(2,3-dihydro-3-hydroxy-3-(meta-trifluoromethylphenyl)-(1H)-isoindol-1-on-2-yl)ethyl]-benzenesulphonamide, m.p.: 230° C. (isopropanol), starting from 3-chloro-3-(meta-trifluoromethylphenyl)-1-(3H)-isobenzofuranone and para-($\beta$-aminoethyl)benzenesulphonamide.

(21) para-[$\beta$-(2,3-dihydro-3-hydroxy-3-(para-chlorophenyl)-(1H)-isoindol-1-on-2-yl)ethyl]benzenesulphonamide, m.p. 230° C. (ethanol), starting from 3-chloro-3-(para-chlorophenyl)-1-(3H)-isobenzofuranone and para-($\beta$-aminoethyl)benzenesulphonamide.

(22) para-[$\beta$-(2,3-dihydro-3-hydroxy-3-(ortho-fluorophenyl)-(1H)-isoindol-1-on-2-yl)ethyl]benzenesulphonamide, m.p.: 120° C. (isopropanol), starting from 3-chloro-3-(ortho-fluorophenyl)-1-(3H)-isobenzofuranone and para-($\beta$-aminoethyl)benzenesulphonamide.

(23) para-[(2,3-dihydro-3-hydroxy-3-phenyl-(1H)-isoindol-1-on-2-yl)methyl]benzenesulphonamide, m.p.: 222° C. (ethyl acetate), starting from 3-chloro-3-phenyl-1-(3H)-isobenzofuranone and para-(aminomethyl)-benzenesulphonamide.

EXAMPLE 24 para-[$\beta$-(2,3-dihydro-3-phenyl-(1H)-isoindol-1-on-2-yl)-ethyl]benzenesulphonamide 12 parts of para-[$\beta$-(2,3-dihydro-3-hydroxy-3-phenyl-(1H)-isoindol-1-on-2-yl)ethyl]benzenesulphonamide are refluxed for 7 hours with 120 parts of 98% formic acid. After concentration in vacuo, the residue is recrystallized in 110 parts of ethyl acetate to give 8 parts of the desired product, m.p.: 218° C.

EXAMPLES 2 TO 35

The following derivatives were prepared according to the method described in Example 24:

(25) para-[β-(2,3-dihydro-3-(para-fluorophenyl)-(1H)-isoindol-1-on-2-yl)ethyl]benzenesulphonamide, m.p.: 192° C. (ethyl acetate), starting from para-[β-(2,3-dihydro-3-hydroxy-3-(para-fluorophenyl)-(1H)-isoindol-1-on-2-yl)ethyl]benzenesulphonamide.

(26) para-[β-(2,3-dihydro-3-phenyl-5-bromo-(1H)-isoindol-1-on-2-yl)ethyl]benzenesulphonamide, m.p.: 245° C. (acetonitrile), starting from para-[β-(2,3-dihydro-3-hydroxy-3-phenyl-5-bromo-(1H)-isoindol-1-on-2-yl)ethyl]benzenesulphonamide.

(27) para-[β-(2,3-dihydro-3-phenyl-5,6dimethoxy-(1H)-isoindol-1-on-2-yl)ethyl]benzenesulphonamide m.p.: 200° C. (acetonitrile) starting from para-[β-(2,3-dihydro-3-hydroxy-3-phenyl-5,6-dimethoxy)-(1H)-isoindol-1-on-2-yl)ethyl]benzenesulphonamide.

(28) para-[β-(2,3-dihydro-3-(2-thienyl)-(1H)-isoindol-1-on-2-yl)ethyl]benzenesulphonamide m.p.: 230° C. (ethyl acetate), starting from para-[β-(2,3-dihydro-3-hydroxy-3-(2-thienyl)-(1H)-isoindol-1-on-2-yl)ethyl]benzenesulphonamide.

(29) para-[β-(2,3-dihydro-3-phenyl-5-methoxy-(1H)-isoindol-1-on-2-yl)ethyl]benzenesulphonamide, m.p.: 204°–205° C. (isopropanol), starting from para-[β-(2,3-dihydro-3-hydroxy-3-phenyl-5-methoxy-(1H)-isoindol-1-on-2-yl)ethyl]benzenesulphonamide.

(30) para-[β-(2,3-dihydro-3-phenyl-5,6-methylenedioxy-(1H)-isoindol-1-on-2-yl)ethyl]benzenesulphonamide, m.p.: 229°–230° C. (DMF/H$_2$O), starting from para-[β-(2,3-dihydro-3-hydroxy-3-phenyl-5,6-methylenedioxy-(1H)-isoindol-1-on-2-yl)ethyl]benzenesulphonamide.

(31) para-[β-(2,3-dihydro-3-(meta-fluorophenyl)-(1H)-isoindol-1-on-2-yl)ethyl]benzenesulphonamide, m.p.: 224° C. (acetonitrile), starting from para-[β-(2,3-dihydro-3-hydroxy-3-(meta-fluorophenyl)-(1H)-isoindol-1-on-2-yl)ethyl]benzenesulphonamide.

(32) para-[β-(2,3-dihydro-3-(meta-trifluoromethylphenyl)-(1H)-isoindol-1-on-2-yl)ethyl]benzenesulphonamide, m.p.: 204° C. (ethyl acetate), starting from para-[β-(2,3-dihydro-3-hydroxy-3-(meta-trifluoromethylphenyl)-(1H)-isoindol-1-on-2-yl)ethyl]benzenesulphonamide.

(33) para-[β-(2,3-dihydro-3-(para-chlorophenyl)-(1H)-isoindol-1-on-2-yl)ethyl]benzenesulphonamide, m.p.: 176°–177° C. (isopropanol), starting from para-[β-(2,3-dihydro-3-hydroxy-3-(para-chlorophenyl)-(1H)-isoindol-1-on-2-yl)ethyl]benzenesulphonamide.

(34) para-[β-(2,3-dihydro-3-(ortho-fluorophenyl)-(1H)-isoindol-1-on-2-yl)ethyl]benzenesulphonamide, m.p.: 220° C. (isopropanol), starting from para-[β-(2,3-dihydro-3-hydroxy-3-(ortho-fluorophenyl)-(1H)-isoindol-1-on-2-yl)ethyl]benzenesulphonamide.

(35) para-[(2,3-dihydro-3-phenyl-(1H)-isoindol-1-on-2-yl)methyl]benzenesulphonamide, m.p.: 202° C. (ethyl acetate), starting from para-[(2,3-dihydro-3-hydroxy-3-phenyl-(1H)-isoindol-1-on-2-yl)methyl]benzenesulphonamide.

EXAMPLE 36

1-{para-[β-(2,3-dihydro-3-hydroxy-3-phenyl-(1H)-isoindol-1-on-2-yl)ethyl]benzenesulphonyl}-3-piperidinourea 0.009 mole of a 3.96N solution of sodium methoxide in methanol is added to 3.5 parts of para-[β-(2,3-dihydro-3-hydroxy-3-phenyl-(1H)-isoindol-1-on-2-yl)ethyl]benzenesulphonamide in solution in 35 parts of dimethylformamide. After concentration in vacuo, 3.8 parts of the sodium salt are obtained.

2.5 parts of 1,1-diphenyl-3-piperidinourea are added while stirring to 3.8 parts of the above salt dissolved in 22 parts of dimethylformamide. The reaction mixture is then heated for one hour at 90°–95° C. After 10 minutes, a precipitate begins to appear. After cooling, the precipitate is suction-filtered, washed with ether and dried. 4.2 parts of the sodium salt are obtained which is suspended in 22 parts of dimethylformamide, acidified with 7.5 parts of N hydrochloric acid and then diluted with 25 parts of water. The precipitate obtained is filtered, washed with water and dried in vacuo; 2.3 parts of the desired products are obtained, m.p. 228° C.

EXAMPLES 37 AND 38

The following derivatives were prepared according to the method described in Example 36:

(37) 1-{para-[β(2,3-dihydro-3-hydroxy-3-(para-fluorophenyl)-(1H)-isoindol-1-on-2-yl)ethyl]benzenesulphonyl}-3-cyclohexylurea, m.p.: 228°–229° C. (ethanol), starting from para-[β-(2,3-dihydro-3-hydroxy-3-(para-fluorophenyl)-(1H)-isoindol-1-on-2-yl)ethyl]benzenesulphonamide and cyclohexyl isocyanate.

(38) 1-{para-[β-(2,3-dihydro-3-hydroxy-3-phenyl-5,6-methylenedioxy-(1H)-isoindol-1-on-2-yl)ethyl]-benzenesulphonyl}-3-piperidinourea, isolated in the form of the sodium salt, m.p.: 260° C., starting from para-[β-(2,3-dihydro-3-hydroxy-3-phenyl-5,6-methylenedioxy-(1H)-isoindol-1-on-2-yl)ethyl]benzenesulphonamide and 1,1-diphenyl-3-piperidinourea.

EXAMPLE 39

1-{para-[β(2,3-dihydro-3-phenyl-(1H)-isoindol-1-on-2-yl)ethyl]benzenesulphonyl}-3-piperidinourea 5.6 parts of 1,1-diphenyl-3-piperidinourea are added to 8 parts of para-[β-(2,3-dihydro-3-phenyl-(1H)-isoindol-1-on-2-yl)ethyl]benzenesulphonamide, in the form of the sodium salt, suspended in 50 parts of dimethylformamide. The reaction mixture is then heated, while stirring, to 90°–95° C. At that temperature, solubilisation occurs, then, after 10 minutes, a new precipitate is formed. After heating for one hour and after cooling, the precipitate is suction-filtered, washed with ether and dried in vacuo. 6.2 parts of the desired product are obtained in the form of the sodium salt, m.p.: higher than 260° C.

EXAMPLES 40 TO 58

The following derivatives were prepared according to the method described in Example 39:

(40) 1-{para-[β-(2,3-dihydro-3-phenyl-(1H)-isoindol-1-on-2-yl)ethyl]benzenesulphonyl}-3-cyclohexylurea, isolated in the form of its sodium salt, m.p.: higher than 260° C., starting from para-[β-(2,3-dihydro-3-phenyl-(1H)-isoindol-1-on-2-yl)ethyl]benzenesulphonamide and cyclohexyl isocyanate.

(41) 1-{para-[β-(2,3-dihydro-3-(para-fluorophenyl)-(1H)-isoindol-1-on-2-yl)ethyl]benzenesulphonyl}-3-cyclohexylurea, m.p.: 142° C. (C$_6$H$_6$/isopropanol), starting from para-[β-(2,3-dihydro-3-(para-fluorophenyl)-(1H)-isoindol-1-on-2-yl)ethyl]benzenesulphonamide and cyclohexyl isocyanate.

(42) 1-{para-[β-(2,3-dihydro-3-phenyl-5-bromo-(1H)-isoindol-1-on-2-yl)ethyl]benzenesulphonyl}-3- piperidinourea, m.p.: 220°–222° C. (dimethylformamide/-H₂O), starting from para-[β-(2,3-dihydro-3-phenyl-5-bromo-(1H)-isoindol-1-on-2-yl)ethyl]benzenesulphonamide and 1,1-diphenyl-3-piperidinourea.

(43) 1-{para-[β-(2,3-dihydro-3-phenyl-5-bromo-(1H)-isoindol-1-on-2-yl)ethyl]benzenesulphonyl}-3-cyclohexylurea, m.p.: 179°–180° C. (ethyl acetate), starting from para-[β-(2,3-dihydro-3-phenyl-5-bromo-(1H)-isoindol-1-on-2-yl)ethyl]benzenesulphonamide and cyclohexyl isocyanate.

(44) 1-{para-[β-(2,3-dihydro-3-phenyl-5,6-dimethoxy-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-phenyl-5,6-dimethoxy-(1H)-isoindol-1-on-2-yl)ethyl]benzenesulphonamide and 1,1-diphenyl-3-piperidinourea.

(45) 1-{para-[β-(2,3-dihydro-3-(2-thienyl)-(1H)-isoindol-1-on-2-yl)ethyl]benzenesulphonyl}-3-piperidinourea, m.p.: 150° C. (acetonitrile), starting from para-[β-(2,3-dihydro-3-(2-thienyl)-(1H)-isoindol-1-on-2-yl)-ethyl]benzenesulphonamide and 1,1-diphenyl-3-piperidinourea.

(46) 1-{para-[β-(2,3-dihydro-3-(para-fluorophenyl)-(1H)-isoindol-1-on-2-yl)ethyl]benzenesulphonyl}-3-piperidinourea, m.p.: 190°–191° C. (isopropanol), starting from para-[β-(2,3-dihydro-3-(para-fluorophenyl)-(1H)-isoindol-1-on-2-yl)ethyl]benzenesulphonamide and 1,1-diphenyl-3-piperidinourea.

(47) 1-{para-[β-(2,3-dihydro-3-phenyl-5-methoxy-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-phenyl-5-methoxy-(1H)-isoindol-1-on-2-yl)ethyl]benzenesulphonamide and 1,1-diphenyl-3-piperidinourea.

(48) 1-{para-[β-(2,3-dihydro-3-phenyl-5,6-methylenedioxy-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-phenyl-5,6-methylenedioxy-(1H)-isoindol-1-on-2-yl)ethyl]benzenesulphonamide and 1,1-diphenyl-3-piperidinourea.

(49) 1-{para-[β-(2,3-dihydro-3-phenyl-5,6-methylenedioxy-(1H)-isoindol-1-on-2-yl)ethyl]benzenesulphonyl}-3-cyclohexylurea, m.p.: 212°–216° C. (isopropanol), starting from para-[β-(2,3-dihydro-3-phenyl-5,6-methylenedioxy-(1H)-isoindol-1-on-2-yl)ethyl]benzenesulphonamide and cyclohexyl isocyanate.

(50) 1-{para-[β-(2,3-dihydro-3-(meta-trifluoromethylphenyl)-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-(meta-trifluoromethylphenyl)-(1H)-isoindol-1-on-2-yl)ethyl]benzenesulphonamide and 1,1-diphenyl-3-piperidinourea.

(51) 1-{para-[β-(2,3-dihydro-3-(meta-trifluoromethylphenyl)-(1H)-isoindol-1-on-2-yl)ethyl]benzenesulfonyl}-3-cyclohexylurea, m.p.: 185° C. (ether), starting from para-[β-(2,3-dihydro-3-(meta-trifluoromethylphenyl)-(1H)-isoindol-1-on-2-yl)ethyl]benzenesulphonamide and cyclohexyl isocyanate.

(52) 1-{para-[β-(2,3-dihydro-3-(para-chlorophenyl)-(1H)-isoindol-1-on-2-yl)ethyl]benzenesulphonyl}-3-piperidinourea, m.p.: 209°–211° C. (acetonitrile), starting from para-[β-(2,3-dihydro-3-(para-chlorophenyl)-(1H)-isoindol-1-on-2-yl)ethyl]benzenesulphonamide and 1,1-diphenyl-3-piperidinourea.

(53) 1-{para-[β-(2,3-dihydro-3-(meta-fluorophenyl)-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-(meta-fluorophenyl)-(1H)-isoindol-1-on-2-yl)ethyl]benzenesulphonamide and 1,1-diphenyl-3-piperidinourea.

(54) 1-{para-[β-(2,3-dihydro-3-(meta-fluorophenyl)-(1H)-isoindol-1-on-2-yl)ethyl]benzenesulphonyl}-3-cyclohexylurea, m.p.: 227° C. (acetonitrile), starting from para-[β-(2,3-dihydro-3-(meta-fluorophenyl)-(1H)-isoindol-1-on-2-yl)ethyl]benzenesulphonamide and cyclohexyl isocyanate.

(55) 1-{para-[β-(2,3-dihydro-3-(ortho-fluorophenyl)-(1H)-isoindol-1-on-2-yl)ethyl]benzenesulphonyl}-3-cyclohexylurea, isolated in the form of its sodium salt, m.p.: higher than 260° C., starting from para-[β-(2,3-dihydro-3-(ortho-fluorophenyl)-(1H)-isoindol-1-on-2-yl)ethyl]benzenesulphonamide and cyclohexyl isocyanate.

(56) 1-{para-[β-(2,3-dihydro-3-(ortho-fluorophenyl)-(1H)-isoindol-1-on-2-yl)ethyl]benzenesulphonyl}-3-piperidinourea, isolated in the form of its sodium salt, m.p.: higher than 260° C., starting from para-[β-(2,3-dihydro-3-(ortho-fluorophenyl)-(1H)-isoindol-1-on-2-yl)ethyl]benzenesulphonamide and 1,1-diphenyl-3-piperidinourea.

(57) 1-{para-[(2,3-dihydro-3-phenyl-(1H)-isoindol-1-on-2-yl)methyl]benzenesulphonyl}-3-cyclohexylurea, m.p.: 226° C. (ethyl acetate); starting from para-[(2,3-dihydro-3-phenyl-(1H)-isoindol-1-on-2-yl)methyl]benzenesulphonamide and cyclohexyl isocyanate.

(58) 1-{para-[(2,3-dihydro-3-phenyl-(1H)-isoindol-1-on-2-yl)methyl]benzenesulphonyl}-3-piperidinourea, m.p.: 228° C. (ethyl acetate), starting from para-[(2,3-dihydro-3-phenyl-(1H)-isoindol-1-on-2-yl)-methyl]benzenesulphonamide and 1,1-diphenyl-3-piperidinourea.

We claim:

1. A compound selected from the group consisting of sulfonylurea compounds of the formula I:

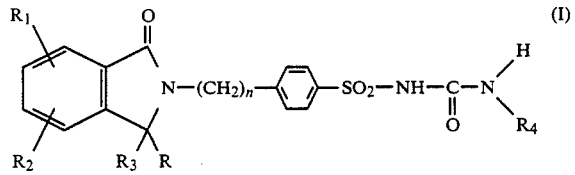

in which n is selected from the group consisting of the integers 1 and 2;

R is selected from the group consisting of: thienyl, furyl, pyridyl radicals and the radical of the formula:

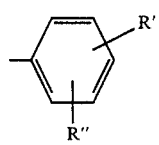

in which R' and R" which are the same or different are each selected from the group consisting of a hydrogen atom, halogen atoms, such as, for example, chlorine, fluorine and bromine atoms, a hydroxy radical, alkyl and alkoxy radicals each having from 1 to 4 carbon atoms inclusive, a trifluoromethyl radical and R' and R" together form a —CH$_2$—O—CH$_2$— group, $R_1$ and $R_2$ which are the same or different are each selected from the group consisting of a hydrogen atom, halogen atoms, such as, for example, chlorine, fluorine and bromine, alkyl and alkoxy radicals each having from 1 to 5 carbon atoms inclusive and a trifluoromethyl radical, and $R_1$ and $R_2$ together form a —CH$_2$—O—CH$_2$— group;

$R_3$ is selected from the group consisting of a hydrogen atom and a hydroxy radical, and $R_4$ is selected from the group consisting of alkyl radicals each having from 1 to 5 carbon atoms, cycloalkyl radicals having from 3 to 8 carbon atoms, azacycloalkyl radicals of the formula:

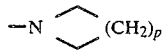

in which p is selected from the group consisting of zero and the integers from 1 to 5, and azabicycloalkyl radicals of the formula:

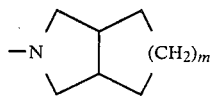

in which m is selected from the group consisting of 1, 2 and 3, and physiologically tolerable basic addition salts thereof.

2. A compound of claim 1 which is 1-{para-[β-(2,3-dihydro-3-phenyl-(1H)-isoindol-1-on-2-yl)ethyl]benzenesulfonyl}-3-piperidinourea and the sodium salt thereof.

3. A compound of claim 1 which is 1-{para[β-(2,3-dihydro-3-(para-fluorophenyl)-(1H)-isoindol-2-yl)ethyl]benzenesulfonyl}-3-cyclohexylurea.

4. A compound of claim 1 which is 1-{para-[β-(2,3-dihydro-3-phenyl-5,6-methylenedioxy-(1H)-isoindol-1-on-2-yl)ethyl]benzenesulfonyl}-3-piperidinourea and the sodium salt thereof.

5. A pharmaceutical composition containing an amount of a compound of claim 1 effective for treating diabetes, together with a a suitable pharmaceutical carrier.

6. A method for treating a living animal body afflicted with diabetes comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,505,921

DATED : March 19, 1985

INVENTOR(S) : Laszlo Beregi, Pierre Hugon, Jacques Duhault and Michelle Boulanger It is certified that error appears in the above-identified patent and that said Letters Patent is hereby corrected as shown below:

Col. 5, line 19; "-2-(3H)-" should read -- -1-(3H)- --

Col. 6, line 8; "dimethyoxy" should read -- dimethoxy --

Col. 6, line 49; "120°C" should read -- 210°C --

Col. 7, line 1; "Examples 2 to 35" should read -- Examples 25 to 35 --

Col. 7, line 15; "5,6dimethoxy" should read -- 5,6-dimethoxy --

Col. 8, line 16; "products" should read -- product --

Signed and Sealed this

Fifteenth Day of October 1985

[SEAL]

Attest:

Attesting Officer

DONALD J. QUIGG

Commissioner of Patents and Trademarks—Designate